(12) United States Patent
Schaaf (10) Patent No.: US 10,863,889 B2
(45) Date of Patent: Dec. 15, 2020

(54) MODULAR ENDOSCOPE

(75) Inventor: Hansgeorg Schaaf, Reichertshausen (DE)

(73) Assignee: Polydiagnost Entwicklungs—, Produktions—, Vertriebs—, Und Service GmbH, Pfaffenhofen (DE)

( * ) Notice: Subject to any disclaimer, the term of this patent is extended or adjusted under 35 U.S.C. 154(b) by 1211 days.

(21) Appl. No.: 12/674,636

(22) PCT Filed: May 15, 2008

(86) PCT No.: PCT/DE2008/000843
§ 371 (c)(1),
(2), (4) Date: May 13, 2011

(87) PCT Pub. No.: WO2009/024107
PCT Pub. Date: Feb. 26, 2009

(65) Prior Publication Data
US 2011/0263933 A1    Oct. 27, 2011

(30) Foreign Application Priority Data

Aug. 23, 2007 (DE) .................. 20 2007 011 781 U
Feb. 27, 2008 (DE) .................. 10 2008 011 387

(51) Int. Cl.
*A61B 1/00* (2006.01)
*A61B 1/012* (2006.01)
(Continued)

(52) U.S. Cl.
CPC .......... *A61B 1/012* (2013.01); *A61B 1/00105* (2013.01); *A61B 1/00142* (2013.01);
(Continued)

(58) Field of Classification Search
CPC .................. A61B 1/00105; A61B 1/00103
(Continued)

(56) References Cited

U.S. PATENT DOCUMENTS

| 4,878,485 A | 11/1989 | Adair |
| 4,977,450 A * | 12/1990 | Yokota ................ H04N 5/2254 348/342 |

(Continued)

FOREIGN PATENT DOCUMENTS

| DE | 19542955 A1 | 5/1997 |
| DE | 19744856 | 4/1999 |

(Continued)

OTHER PUBLICATIONS

Flexible Ureteropyeloscopy with Modular, 'Disposable' Endoscope; Demetrius H. Bagley, M.D.; Department of Urology, Jefferson Medical College of Thomas Jefferson University, Philadelphia, Pennsylvania.

(Continued)

*Primary Examiner* — Alexandra L Newtown
*Assistant Examiner* — Rynae Boler
(74) *Attorney, Agent, or Firm* — Boyle Fredrickson S.C.

(57) ABSTRACT

Disclosed is a modular endoscope system in which a plurality of connecting pieces, tools, and cannulas which are selected according to the use thereof are assigned to a single optics. The connecting pieces and the cannulas are preferably designed for single use, so that merely the optics has to be decontaminated.

26 Claims, 7 Drawing Sheets

(51) Int. Cl.
  *A61M 25/00* (2006.01)
  *A61B 1/313* (2006.01)
  *A61M 25/06* (2006.01)
  *G02B 23/24* (2006.01)

(52) U.S. Cl.
  CPC ............. *A61B 1/313* (2013.01); *A61M 25/00* (2013.01); *A61B 1/00165* (2013.01); *A61M 25/06* (2013.01); *G02B 23/2461* (2013.01); *G02B 23/2476* (2013.01)

(58) Field of Classification Search
  USPC ................. 600/104, 121–125, 170, 172, 133
  See application file for complete search history.

(56) References Cited

U.S. PATENT DOCUMENTS

| | | | |
|---|---|---|---|
| 4,987,884 A * | 1/1991 | Nishioka et al. | 600/181 |
| 5,048,923 A * | 9/1991 | Tsumanuma | C03B 37/01214 385/117 |
| 5,152,277 A * | 10/1992 | Honda | A61B 1/00082 600/106 |
| 5,191,388 A * | 3/1993 | Kilham | G01N 15/0227 250/227.28 |
| 5,222,953 A * | 6/1993 | Dowlatshahi | 606/15 |
| 5,297,310 A * | 3/1994 | Cox et al. | 15/106 |
| 5,301,061 A | 4/1994 | Nakada et al. | |
| 5,607,386 A * | 3/1997 | Flam | 600/120 |
| 5,735,792 A | 4/1998 | Vanden Hoek et al. | |
| 6,006,002 A * | 12/1999 | Motoki | G02B 23/2476 385/117 |
| 6,007,481 A * | 12/1999 | Riek | A61B 1/00165 600/104 |
| 6,007,531 A * | 12/1999 | Snoke et al. | 606/15 |
| 6,017,322 A | 1/2000 | Snoke et al. | |
| 7,654,989 B2 * | 2/2010 | Knapp | 604/284 |
| 7,857,757 B2 * | 12/2010 | Schaaf | 600/182 |
| 2004/0064021 A1 | 4/2004 | Pfeiffer | |
| 2004/0267213 A1 | 12/2004 | Knapp | |
| 2005/0192479 A1* | 9/2005 | Forster | G02B 23/26 600/182 |
| 2006/0252992 A1* | 11/2006 | Mitsumori | A61B 1/005 600/139 |

FOREIGN PATENT DOCUMENTS

| | | |
|---|---|---|
| DE | 19956516 | 6/2001 |
| DE | 10256673 A1 | 6/2004 |
| DE | 10 2004 055412 A1 | 5/2006 |
| DE | 202006006322 U1 | 7/2006 |
| DE | 202006008061 | 9/2006 |
| DE | 102006022827 A1 | 12/2006 |
| DE | 102005018825 B3 | 1/2007 |
| DE | 202007011781 | 11/2007 |
| DE | 102008011387 A1 | 2/2009 |
| WO | 03082394 | 10/2003 |
| WO | WO2006027136 | 3/2006 |

OTHER PUBLICATIONS

Database Medline US NLM3824726; XP002497824 & Urology ISSN: 0090-4295.
Urology, Mar. 1987, Bd. 29, No. 3, Mar. 1987, pp. 296 to 300, ISSN: 0090-4295.
International Search Report, dated Nov. 18, 2008.
Office Action of Priority DE 10 2008 011 387.5, dated Feb. 11, 2014.

* cited by examiner

MODULAR ENDOSCOPE

The invention relates to a modular endoscope in accordance with the preamble of claim 1.

BACKGROUND OF THE INVENTION

Field of the Invention

Endoscopy has well established itself in minimally invasive surgery. Endoscopes are used for diagnostics and therapy and for endoscopes designed with catheter probes. Endoscopes used in diagnostics and therapy comprise a cannula or probe having optics inserted for light and image transmission and being designed with further connections, for instance, a rinsing connection for supplying rinsing fluid, or a working connection for attaching a tool, for instance, a drill, biopsy forceps, or a laser beam conductor for surgical or therapeutic treatment. These known endoscopes are optimized with regard to their respective field of use, for instance, the endoscopy of small joints (temporomandibular joint, ankle joint, toe joint, knuckle), root canal endoscopy, milk canal endoscopy, periodontal pocket endoscopy, tear duct endoscopy, intervertebral disk endoscopy, or spinal canal endoscopy, wherein the outer diameter lies, depending on the range of use, between 0.3 mm (glaucoma diagnostics) up to the range of several millimeters with catheter probes. Such kind of endoscopes are, for instance, disclosed in DE 20 2006006 322 U1, DE 195 42 955 C2, or DE 10 2005 018 825 B3, all of which are by the applicant.

A large problem in medical technology, especially also with endoscopy, is the decontamination of the instruments. Presently, in the case of examinations of hepatitis-B, AIDS, or Kreuzfeld Jakob patients, the endoscopes are destroyed after the examination. Otherwise, a careful sterilization of the surgical and diagnostic instruments is necessary so as to kill or remove microorganisms or other impurities on the surface of the instruments. A problem is here in particular the cleaning of the coupling elements or of the working channels for connecting the rinsing pipe or the tools since they are only hard to access due to the small diameters and the complex geometry. Basically, three procedure variants are available for the decontamination of endoscopes:
  a) autoclaving
  b) ethylene oxide sterilization, and
  c) plasma sterilization.

A problem with the autoclaving of endoscopes consists in that, due to the high temperatures (>130° C.), a clouding of the optics for image transmission may occur, resulting from the condensing of carbon molecules dissolved away during autoclaving.

The afore-mentioned ethylene oxide sterilization is practically no longer used today in hospitals and medical practices since, on the one hand, the sterilization takes very long time and, on the other hand, a ventilation phase of several hours is required to eliminate toxic residues.

Recently, plasma sterilization has therefore become accepted, wherein the microorganisms are killed by the formation of highly reactive hydroxy and hydroxyl radicals from hydrogen peroxide. This sterilization process takes place in vacuum at a comparatively low temperature (approximately 45° C.), so that no thermal damage to the optics occurs. It is, however, a disadvantage of this method that cannulas or probes with lumens of a length less than 0.3 cm and more than 30 cm cannot be sterilized with sufficient reliability since it is not ensured with such lumens with a small diameter/length ratio that the hydrogen peroxide vapor may be supplied into the entire lumen space for sterilization.

Another problem of conventional endoscopes consists in that they are—as explained before—optimized with regard to the respective application. In so doing, for instance, it is necessary to provide for therapeutic endoscopy, depending on the instrumentation, endoscopes with different probe and cannula diameters, so that substantial investment costs will accrue.

SUMMARY OF THE INVENTION

In contrast to this it is an object of the invention to provide an endoscope that is, on the one hand, most easy to decontaminate and that enables, on the other hand, a wide range of application.

This object is solved by a modular endoscope with the features of claim 1.

The modular endoscope comprises optics for image transmission which is adapted to be detachably connected with a cannula. The modular endoscope furthermore comprises a plurality of disposable cannulas designed with different diameters and connections, depending on a diagnostic or therapeutic application. This means, depending on the application and the instrumentation it is possible to attach a suitable cannula to the optics. These cannulas are destroyed after use, so that merely the optics has to be decontaminated. The optics has no inner dimensions that are critical for plasma sterilization, but only a smooth outer surface, so that it is possible to perform the decontamination in a very reliable manner and with little effort pursuant to a plasma sterilization method at low temperature and without any thermal damages.

A mechanical damage to the optics by external influences may almost be excluded by a mounted protective pipe.

By an appropriate design of the length of the protective pipe and of the diameter of the protective pipe it is guaranteed that the optics can be decontaminated during plasma sterilization.

In one embodiment of the modular endoscope, the cannulas selected depending on the case of application may be attached exchangeably to disposable multi-port connecting pieces comprising a connection for the optics and further connections, for instance, for a rinsing device, a tool, or the like. The connecting pieces may be designed as a Y-piece with an axial connection and a connection inclined thereto, wherein the axial connection, as a rule, is the optics connection.

In the case of applications requiring an instrumentation, a disposable connecting piece is provided, wherein an axial connection and two lateral connections arranged in a way inclined thereto are provided, one of the lateral connections being the optics connection and the axial connection being a working connection for attaching a tool.

For attaching working shafts of large diameter it is preferred to provide the multi-port connecting pieces with an additional suitable coupling, for instance, a Luer Lock, via which it is possible to attach the modular endoscope to the working shaft.

Since the length of the cannula may change depending on the case of application, but since the same optics is always used, adjustment means may be used in accordance with the invention via which it is possible to align the optics with respect to the cannula/working shaft orifice.

In the transition area from the coated portion of the optics to that end portion that is accommodated in the cannula, a guiding pipe is provided along which the adjustment means is adapted to be displaced.

In the case of very short cannulas the adjustment means may additionally be designed with a distance piece inserted between the connecting piece and the actual, displaceable adjustment means. Such a distance piece may, for instance, be used with cannulas for vitrectomy which are relatively short and curved.

This distance piece may also be designed integral with the connecting piece.

In a variant of the endoscope the cannula is designed as biopsy forceps, wherein a forceps head is attached to a distal end of a cannula said forceps head being adapted to be actuated by means of an actuating wire guided in the cannula.

The actuation of the forceps head is preferably performed via actuation means adapted to be detachably attached to the actuating wire, so that the cannula may, for instance, be attached to a connecting piece, and subsequently the actuation means is connected with the actuating wire and supported at the connecting piece.

In an alternative variant, the cannula may be provided with an external receiver element for a tool.

This receiver element is preferably attached to the distal end of the cannula.

For therapeutic treatments by means of laser energy it is possible to insert laser optics into the cannula and to adjust it by means of a laser shifter with respect to the distal end of the cannula.

The optics used with the endoscope according to the invention may also be designed as an image sensor, so that it is possible to transmit image signals like a video camera.

In one embodiment it is preferred to guide the optics such that it is adapted to be moved out of the cannula, for instance, into a canal, so that monitoring is simplified during a treatment with a drill or the like.

The modular endoscope is preferably also designed with a brush for cleaning the components, in particular small lumens.

In one variant, a slightly ground trocar is provided which is adapted to be inserted in a cannula of the modular endoscope and which is extracted after the positioning of the cannula and is replaced by optics or the like.

In one embodiment of the invention it is provided to assign cannulas with diameters of 0.5 mm, 0.95 mm, 1.1 mm, 1.6 mm, and 2.0 mm or more to optics, so that a plurality of endoscopy applications are covered.

The optics is preferably designed with light conductors and image conductors, wherein the image conductors are connected with a modular ocular via an ocular connection (cf. German patent application Wechselokular [exchange ocular] DE 102 56 673.9), and wherein the light conductors are connected to a light source via a light connection.

The proximal end of the endoscope cannula may also be provided with a Luer Lock connection or a bayonet connection to which a working shaft may be connected. The endoscope cannula is inserted into this working shaft and is fixedly connected with the endoscope cannula by means of a male or a female Luer Lock or bayonet fastener. Prior to this procedure, the working shaft was placed in a small joint, for instance, by means of a trocar. Prior to the insertion of the endoscope cannula the trocar will be removed from the working shaft, as a matter of fact.

In the case of therapeutic applications, for instance, during the treatment of small joints, it is possible to insert a trocar that has been slightly ground in an oblique manner into the cannula. After the positioning of the cannula the trocar is extracted and the afore-described optics is inserted.

In the modular endoscope according to the invention it is intended to provide the cannula and the connecting pieces in a sterile package, wherein the decontamination is in this case performed preferably at the factory by means of gas sterilization.

Other advantageous further developments of the invention are the subject matter of further subclaims.

BRIEF DESCRIPTION OF THE DRAWINGS

In the following, a preferred embodiment of the invention will be explained in detail by means of schematic drawings. There show.

DETAILED DESCRIPTION OF THE PREFERRED EMBODIMENTS

Figure 1:
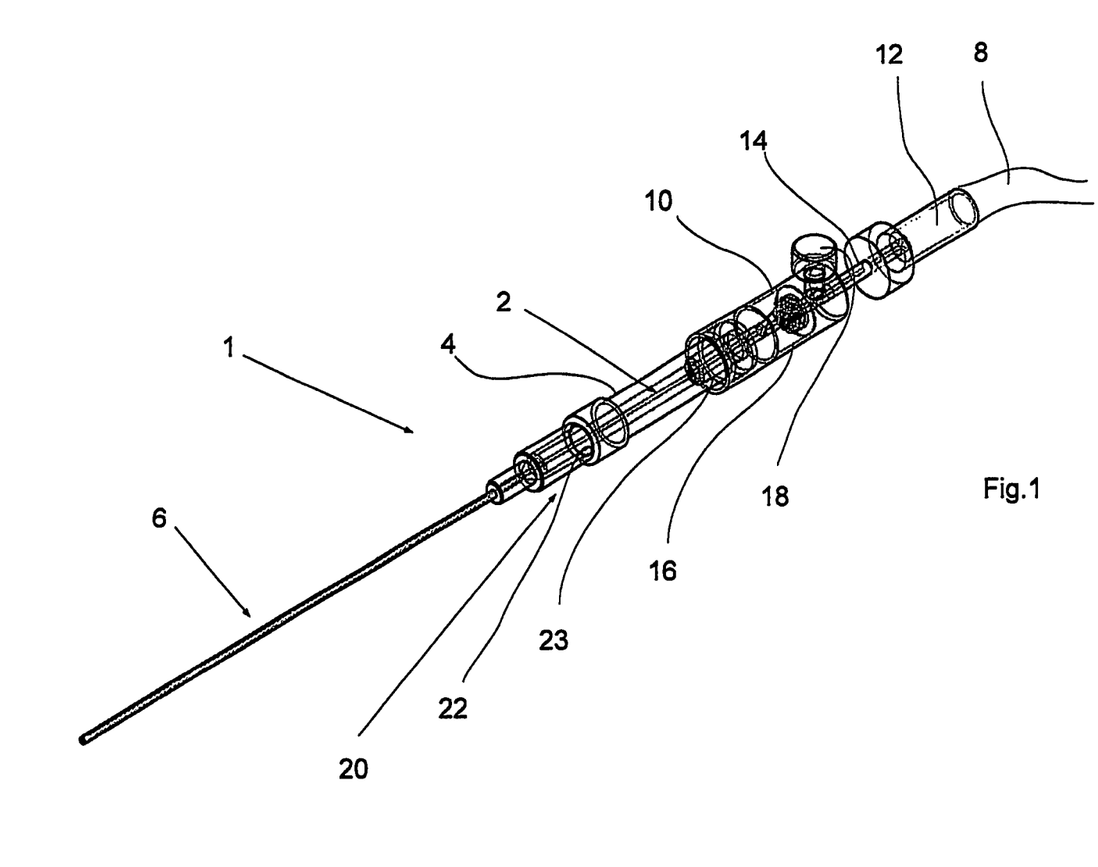
FIG. 1 a three-dimensional schematic diagram of an endoscope according to the invention.

FIG. 1 shows a schematic three-dimensional representation of a modular rigid semi-flexible endoscope 1 that is composed, depending on the intended purpose, of the endoscope modules described in more detail in the following. Such an endoscope 1 consists substantially of optics 2 which is attached to a cannula 6 by means of a connecting piece 4. The optics 2 consists in a per se known manner of a highly flexible bundle of regular image and light fibers by which a region to be examined is illuminated and image information is transmitted to an ocular or a connected image recording device. This optics 2 may be designed with a resolution of between 3,000 and 50,000 pixels with respect to the applications intended. The rear region of the optics 2 which extends away from the connecting piece 4 towards an ocular adapted to be decoupled and not illustrated in FIG. 1, which may, for instance, also be designed as a zoom ocular, is provided with a protective pipe 8 protecting this portion from external influences. In the region of the cannula the protective pipe 8 is crosscut, so that the image and light fibers accommodated in a sheath protrude. The distal end portion of the optics 2 which faces the region to be observed is provided with a lens system and sealed by means of a diamond glass disk, so that the interior of the optics cannot be contaminated during the examination. With respect to the construction of such optics reference is, for instance, made to the initially mentioned DE 10 2006 022 827 A1.

The cannula 6 accommodating the end portion of the optics 2 is either manufactured of stainless steel or of a flexible plastic material, wherein the user may choose between cannulas in the diameter range of 0.95 mm to 2.0 mm or more. In the described embodiment the optics 2 is designed with an outer diameter of approximately 0.5 mm, preferably 0.53 mm. This very small diameter enables the use of the endoscope 1, for instance, in the tear duct, in the milk duct (early recognition of cancer), in the root canal, or in the saliva canal.

The connection between the optics 2 and the cannula 6 is performed via the connecting piece 4 that is designed as a one-port connection in the embodiment pursuant to FIG. 1. In the modular endoscope 1 it is provided that a plurality of different cannulas 6 and connecting pieces 4 is assigned to one single optics 2. The basic adjustment with respect to the length of the optics and the length of the cannula is preformed by a suitable crosscutting of the protective pipe 8 which is easy to perform even for a layman. The precise length adjustment is then performed by an adjustment means referred to as shifter 10 in the following. The basic construction of such a shifter 10 is, for instance, described in DE 10 2005 08 825 B3, so that only the elements important for understanding will be described here. The shifter 10 is attached to the optics 2, more exactly to the protective pipe 8, via a bend protection connection 12 and comprises a guiding pipe 14 enclosing the optics 2, along which a sliding piece 16 connected with the cannula 6 is guided in a displaceable manner. It is adapted to be fixed on the guiding pipe 14 by means of a locking screw 18, so that the optics 2 is adapted to be shifted correspondingly inside the cannula 6 until the distal end of the optics 2 is aligned with respect to the cannula orifice. The locking screw 18 is then tightened to fix this relative position. In the embodiment illustrated, the cannula 6 is detachably attached to a cannula connection 22 via a coupling 20. The connecting piece 4 is detachably connected with the shifter 10 via a suitable coupling 23. Luer couplings may, for instance, be used for the couplings 22, 23.

As already mentioned, diameter, length, and material of the cannula 6 may be chosen from the module assembly set in dependence of the intended purpose. As will be explained in more detail in the following, both the cannula 6 and the connecting piece 4 are designed as disposable components and are delivered in a sterile package and disposed of after single use. Accordingly, only the optics 2 has to be decontaminated.

Figure 2:
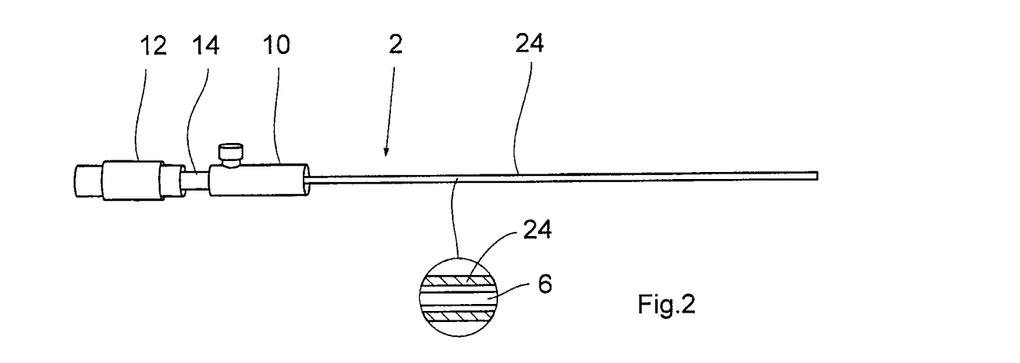
FIG. 2 a monograph of optics of the endoscope of FIG. 1.

FIG. 2 shows a partial illustration of the optics 2 of FIG. 1 with the bend protection connection 12, the guiding pipe 14, the shifter 10, and the projecting distal end portion of the optics 2 which is accommodated in the cannula 6 and in the connecting piece 4 in FIG. 1. In the detailed illustration pursuant to FIG. 2 a protective pipe 24 is slid on for the protection of the sensitive image and light conductors and of the diamond glass disk and the lens arrangement. It extends across the entire length of the distal end portion of the optics 2, so that damaging is excluded.

The protective pipe 24 is manufactured of a metal material in the illustrated embodiment and remains on the distal end portion of the optics 2 during storing, transportation, and also decontamination. The inner diameter and the length of the protective pipe 24 are chosen such that a plasma sterilization by hydrogen peroxide may be performed.

Figure 3:
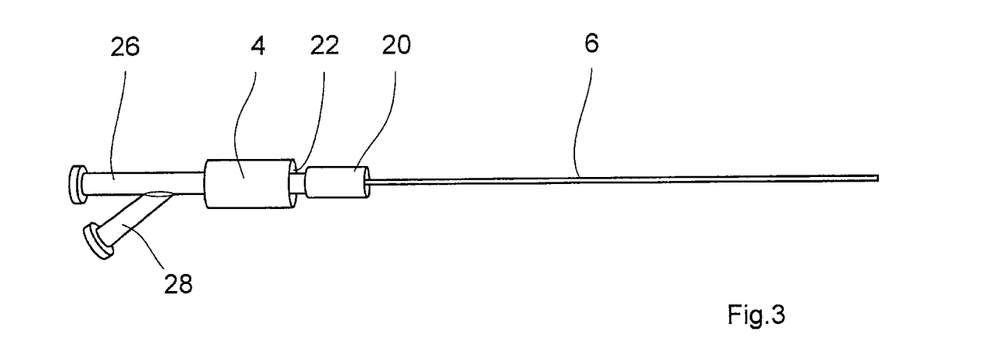
FIG. 3 a diagnostic cannula of the modular endoscope.

For attaching a cannula 6 to the sterilized optics 2, the protective pipe 24 is first of all removed and the distal end portion of the optics 2 is inserted into a cannula 6. FIG. 3 shows an embodiment of a diagnostic cannula 6 attached via a Luer coupling 20 to the cannula connection 22 of a connecting piece 4 designed with an axial connection or outlet 26 and an inclined connection 28. In such a diagnostic cannula 6 the optics 2 is preferably inserted in the axial connection 26 while the connection 28 serves to connect a rinsing agent pipe.

The diameter of the cannula 6 is adapted to the respective case of application. In the illustrated embodiment the connecting piece 4 is manufactured of a plastic material while the cannula 6 and the cannula-side portion of the coupling 20 (Luer Lock) are manufactured of steel.

Figure 4:
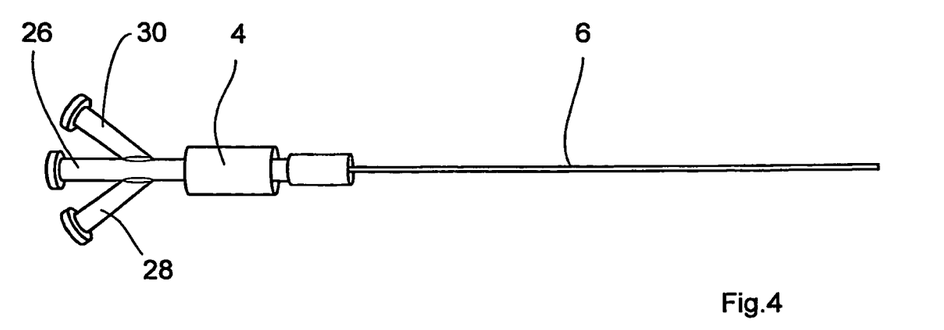
FIG. 4 a therapeutic cannula of the modular endoscope of FIG. 1.

FIG. 4 shows an embodiment of a therapeutic cannula in which the connecting piece 4 is designed with three connections: an axial connection 26, an inclined connection 28, and a further inclined connection 30 arranged symmetrically thereto. In this variant the optics 2 is inserted in one of the inclined connections 28, 30. By means of the central axial connection 26 it is, for instance, possible to attach a tool, such as biopsy forceps, a small basket for removing stones, or a micro drill as described in DE 197 44 856. A rinsing pipe may again be connected to the remaining inclined connection 28, 30.

As for the rest, the cannula pursuant to FIG. 4 corresponds to that of FIG. 3, so that further explanations are dispensable.

Figure 5:
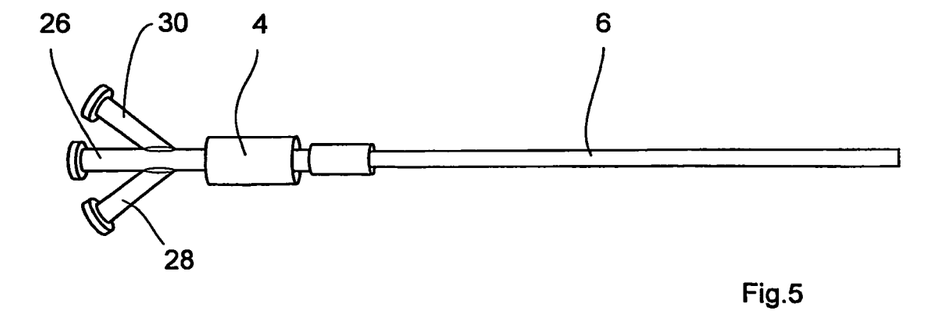
FIG. 5 a therapeutic cannula with a larger diameter than that of FIG. 4.

FIG. 5 shows a variant of the therapeutic cannula pursuant to FIG. 4, wherein a cannula 6 with a substantially larger diameter than in the embodiment pursuant to FIG. 4 is attached to the connecting piece 4 with the three outlets or connections 26, 28, 30. The larger cannula diameter enables, for instance, the use of a larger tool.

Figure 6:
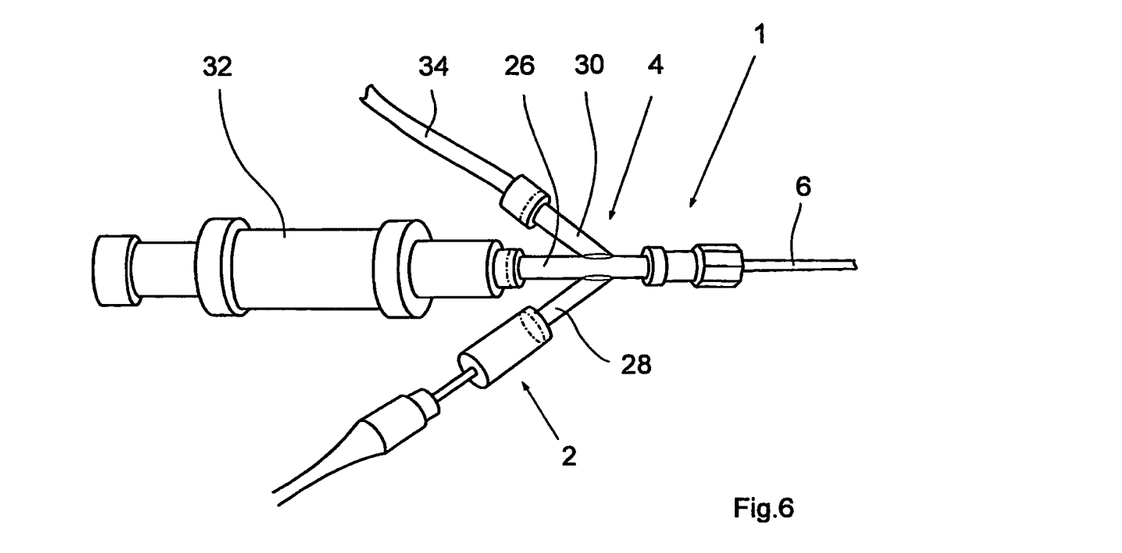
FIG. 6 an example of an endoscope designed with the therapeutic cannula pursuant to FIGS. 4 and 5.

FIG. 6 shows a partial illustration of an endoscope 1 that is designed as a therapeutic probe 1 by combining the optics of FIG. 2, a cannula 6, and a connecting piece 4 pursuant to FIG. 4. This embodiment reveals that the optics 2 is connected to the inclined connection 28. This is only possible since, in the modular system described, the optics 2 is designed so flexible that it is adapted to be inserted through the inclined connection 28 into the cannula 6 without any damage. To this end, the connecting piece 4 is designed with a smooth surface at least in the area between the inclined connection 28 and the following axial region, so that the optics 2 is adapted to be inserted in a sliding manner. In this embodiment, a drilling tool 32 is attached to the central axial outlet 26. A rinsing pipe 34 is connected to the further inclined connection 30.

Figure 7:
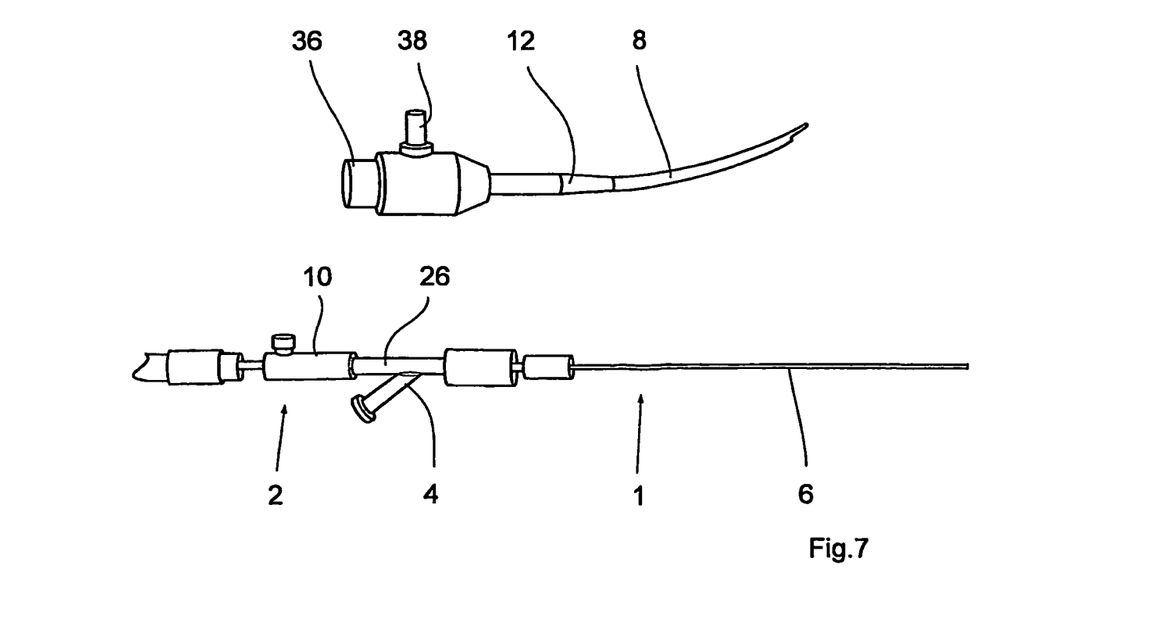
FIG. 7 an embodiment of a diagnostic endoscope with a cannula pursuant to FIG. 2.

FIG. 7 shows a partial illustration of a diagnostic endoscope 1 with a cannula 6 and a connecting piece 4 pursuant to FIG. 3, wherein the optics 2 is inserted in the axial outlet 26 and is aligned with respect to the orifice of the cannula 6 by means of the shifter 10. The region of the optics 2 which follows the shifter 10 to the rear, away from the cannula 6, is—as explained before—coated with the protective pipe 8. The end portion of the optics 2 spaced apart from the cannula 6 is, via a further bend protection connection 12, connected to an ocular coupling 36 at which an illumination connection 38 for the light conductors of the optics 2 is also provided. Via the ocular coupling 36 the optics 2 is adapted to be attached to an ocular, for instance, a zoom ocular. This zoom ocular enables the optics 2 despite the small outer diameter of 0.53 mm to represent the image with a sufficient diameter of more than 11 cm, wherein moiré effects may be suppressed by suitable filters.

As a matter of principle it is intended in the modular endoscope system according to the invention to throw the cannulas 6 and the connecting pieces 4 away after each use since, especially with cannulas of a small diameter, a decontamination by plasma treatment is not possible due to the very small lumen diameter. For particular applications the modular system also intends to provide cannulas 6 and connecting pieces 4 of the afore-described construction which are reusable and which are manufactured of a material adapted to be autoclaved.

In the described embodiment it is also intended to provide, both at therapeutic and at diagnostic connecting pieces 4 a further, axial Luer Lock at the side of the cannula. It has a larger diameter than the coupling 20 (see FIG. 3) via which the cannula 6 is attached to the connecting piece 4. This additional Luer Lock enables to attach the endoscope 1 to a working shaft with a comparatively very large diameter. Thus, for instance, in arthroscopy such a working shaft with a comparatively large diameter is inserted along with a trocar into the joint to form an aperture for inserting the endoscope. After the positioning of the working shaft in the joint, the trocar is extracted—the working shaft remains in the joint. Subsequently, the endoscope 1 is attached and connected with the working shaft via the additional Luer Lock.

During the operation on smaller joints it is possible to insert a comparatively small, slightly ground trocar into the cannula 6. After the positioning of the cannula 6 by means of the trocar in the joint, the trocar is extracted from the cannula 6, and the afore-described optics 2 as well as the operation tool, for instance, a drill or a fiber strand for the transmission of laser light, or the like is inserted into the cannula 6 via the connecting piece 4.

In particular therapies, for instance, in vitrectomy, cannulas are used which are substantially shorter vis-à-vis the "standard" optics 2, so that the shifter 10 does not suffice to produce a length adjustment. In this case, a distance piece (not illustrated) may be inserted between the connecting piece 4 and the shifter 10, the length of which is chosen such that the resulting length of the, for instance, curved cannula and the distance piece corresponds approximately to the length of an afore-described cannula 6—the position of the optics 2 may then, as described before, be adjusted via the shifter 10.

Figure 8:
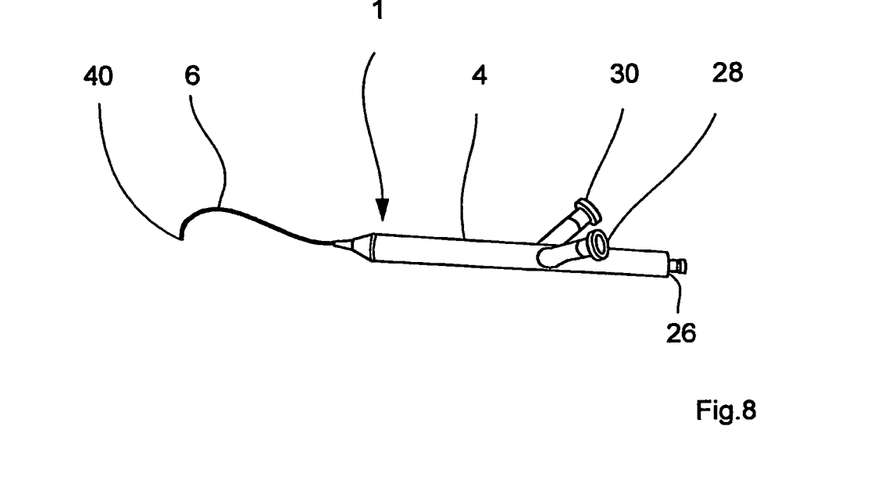
FIGS. 8 to 11 an embodiment of a cannula with an externally attached tool.

By means of FIGS. 8 to 11 an embodiment of the modular endoscope 1 with a curved cannula 6 is explained as it may, for instance, be used in tooth root treatment. In the case of such a tooth root treatment a drilling tool is positioned in the root canal by means of the afore-described optics 2. As a matter of principle, a curved therapeutic cannula may be used for such treatment, the construction of which is performed in accordance with the afore-described embodiments. Like in the embodiment pursuant to FIG. 4 it is then, for instance, possible to attach a micro drill to an axial connection 26 while the optics and a rinsing pipe are connected to the inclined connections 28, 30. FIG. 8, however, shows an embodiment in which the tool is fixed at the outside of the cannula 6.

In this endoscope a curved short cannula 6 is attached to a connecting piece 4 with an axial connection 26 and two inclined connections 28, 30 which are arranged in a V-shaped manner with respect to each other and facing upwards in the illustration pursuant to FIG. 8. This connecting piece 4 has a larger axial length than that of the afore-described embodiments, so that the shorter axial length of the curved cannula 6 is compensated for. At the distal end portion of the curved cannula 6, a receiver element 40 for the external attachment of a tool, for instance, a nickel titanium drill as it is commonly used for root canal treatments, is provided.

Figure 9:
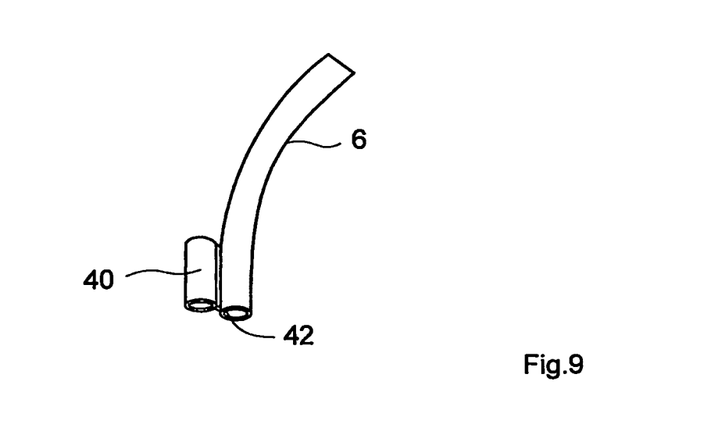
Figure 10:
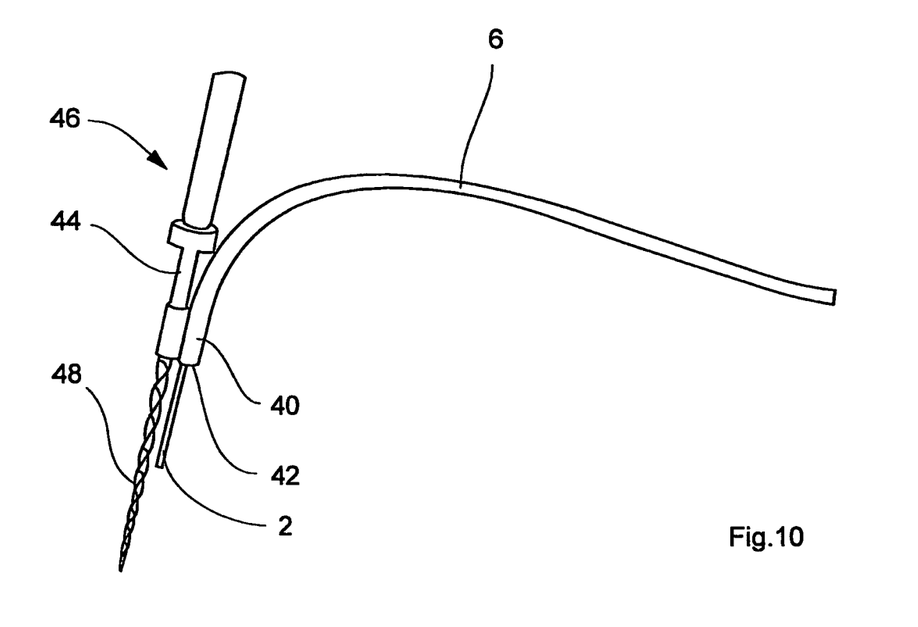

This distal end portion of the cannula 6 is illustrated to a larger scale in FIG. 9. Accordingly, in the orifice region 42 of the cannula 6 the receiver element 40 that is roughly sleeve-shaped in this embodiment is attached, for instance, by soldering or the like, wherein the sleeve axis and the axis of the cannula orifice region 42 extend approximately at parallel distance or somewhat inclined to each other. As illustrated in FIG. 10, a stationary shaft 44 of a drilling tool 46 that is driven pneumatically, hydraulically, or electrically may be arranged in this receiver element. A drill 48 of the drilling tool 46 may then be positioned in the root canal by means of the optics 2 inserted in the cannula 6 via the axial connection 26.

Figure 11:
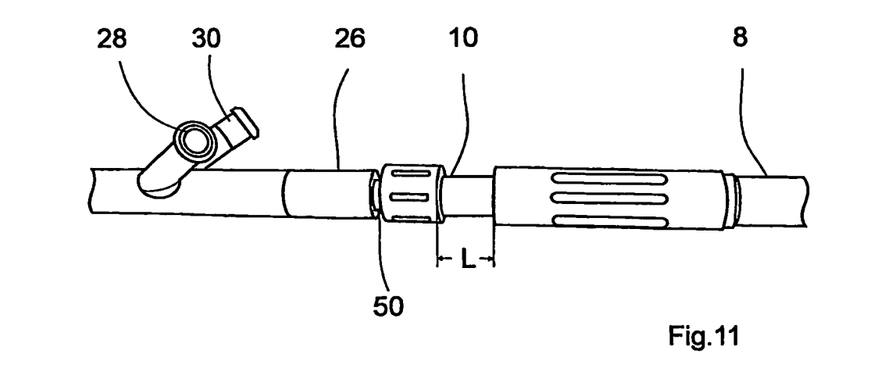

According to FIG. 11, the adjustment of the optics 2 is performed with respect to the orifice region 42 of the cannula 6—similar as with the afore-described embodiments—via a shifter 10 attached to the axial connection 26. The adjustment length L indicated in FIG. 11 may be set via an adjusting screw 50 to position the optics 2 with respect to the orifice region 42. According to FIG. 10, the optics 2 need not terminate with the orifice region 42, but may, for instance, be pushed into the root canal during the root treatment by adjusting the shifter 10, so that the exact operating position of the drill 48 may always be watched. This means that the endoscope according to the invention enables a variable positioning of the optics 2 during the treatment.

As a matter of fact, this variable positioning is also possible if the drilling tool is guided through the cannula 6.

In the afore-describe embodiments, glass fiber optics is preferably used. As a matter of principle, however, image sensors such as they are, for instance, applied in video technology (CCD sensors, CMOS sensors, or the like) may also be used.

As explained initially, curved cannulas 6 are, for instance, used in vitrectomy, wherein a diode laser is then used as a tool and the laser beam is guided via glass fibers to the region to be treated. For positioning this glass fiber strand, a laser shifter as described in DE 199 56 516 is, for instance, used.

Figure 12:
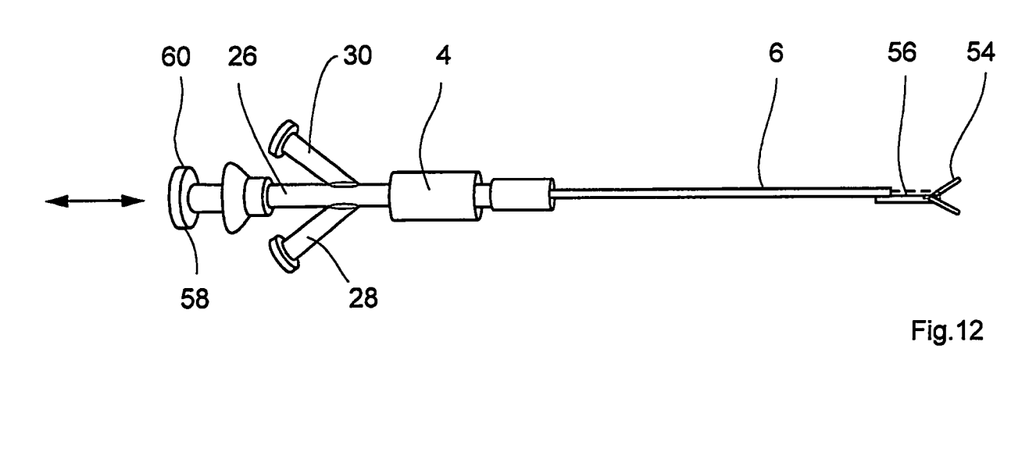
FIG. 12 an embodiment of an endoscope with a cannula designed as biopsy forceps.

FIG. 12 shows an embodiment in which biopsy forceps are used as a tool. Conventional biopsy forceps as described, for instance, in DE 20 2006 008 061 U1 have a comparatively large diameter of at least 0.8 millimeters, so that it is practically impossible to insert these biopsy forceps along with an optics 2 in a cannula 6 of the modular endoscope according to the afore-described embodiments since the total diameter of the cannula 6 would then be substantially too large for a plurality of treatments.

This disadvantage is overcome in the modular endoscope 1 according to the invention in that a cannula 6 is designed with biopsy forceps. Such a biopsy cannula is illustrated in FIG. 12. Here, a biopsy forceps head 52 is attached to a conventional, straight cannula 6 with a diameter of approximately 1.1 millimeters (or less), for instance, by soldering or the like. In the illustrated embodiment this forceps head 52 is fastened laterally at the distal end of the cannula 6. The actuation of forceps jaws 54 (for instance, spoons) for taking a tissue sample is performed via an actuation wire 56 indicated by dashes in FIG. 12 which extends through the cannula 6 and the connecting piece 4 as well as the axial connection 26 to an actuation means 58. In the position illustrated in FIG. 12 a spring-biased actuation element 60 is moved to the right against the spring force, so that the forceps jaws 54 open in a V-shaped manner. On release of the actuation element 60 the forceps jaws 54 close, so that the tissue sample may be taken. This means that in this embodiment according to the invention the function of a spiral-shaped metal support pipe used with conventional biopsy forceps is taken over by the cannula 6, so that the biopsy forceps can easily be attached to a connecting piece 4 of the modular endoscope 1. For attaching this biopsy cannula to the connecting piece 4 the actuation means 58 may be detached from the actuation wire 56, so that the end portion thereof that is remote from the forceps jaws 54 is adapted to be guided through the axial connection 26 when the cannula 6 is attached to the connecting piece 4, and the actuation means 58 is subsequently, for instance, by screwing or clamping, connected with the actuation wire 56. The optics 2 may then again be inserted through one of the lateral connections 28, 30.

The afore-described biopsy cannula is preferably manufactured of metal and may be autoclaved or sterilized in another manner without major problems.

In a case in which elements of the modular endoscope are to be decontaminated, this system includes cleaning brushes that are adapted to the respective geometry in order to also clean regions that are hard to access or small lumens, respectively.

The afore-described modular concept according to the invention enables almost any instrumentation with one single optics and different disposable cannulas/working shafts. It is possible to implement different working lengths of the endoscope in a simple manner by elongating or shortening the external protective pipe. The users are thus enabled to work in an interdisciplinary manner and to also use working instruments from other special fields by a simple adaptation of the endoscope. The single use of cannulas 6 and connecting pieces 4 and the simple sterilization of the optics 2 ensure a decontamination of the endoscope in an exemplary manner, wherein the effort for the users is minimal, so that also the investment costs are substantially smaller vis-à-vis conventional solutions.

Disclosed is a modular endoscope system in which a plurality of connecting pieces, tools, and cannulas which are selected according to the use thereof are assigned to a single optics. The connecting pieces and the cannulas are preferably designed for single use, so that merely the optics has to be decontaminated.

The applicant reserves the right to direct own, independent claims to the individual embodiments of the described endoscope modules. This means that each of the embodiments illustrated in the Figures may be made the subject matter of an own, independent patent application.

The invention claimed is:

1. A modular rigid endoscope comprising
an optics cannula manufactured from a rigid material with optics comprising a bundle of image and light fibers guided through an interior thereof for image transmission,
   wherein a distal end of said optics is provided with a lens system and seal by means of a diamond glass disk,
   wherein the optics is detachably connected with the optics cannula by means of a coupling;
a plurality of disposable, sterilized cannulas or working shafts which are designed with different diameters greater than 0.5 mm, and/or connections depending on a diagnostic or therapeutic application; and
an adjustment means is provided for positioning lens-side end portions of said optics with respect to a cannula/working shaft orifice, wherein said adjustment means is, on the one hand, connected with at least one of said cannulas or working shafts and, on the other hand, with said optics, said adjustment means comprising
   a guiding pipe enclosing a protective pipe of said optics along which a sliding piece connected with the optics cannula is guided in a displaceable manner to position the optics and lens system within the optics cannula,
   said optics having an outer diameter of about 0.5 mm, and comprising light conductors and image conductors.

2. The endoscope according to claim 1, wherein a protective tube is placed on an uncoated end portion of said optics.

3. The endoscope according to claim 2, wherein the length of the protective tube and the inner diameter of the protective tube are designed such that a plasma sterilization is possible.

4. The endoscope according to claim 1, comprising a disposable multi port connecting piece to which the optics cannula is adapted to be attached exchangeably, and which comprises a plurality of connections for said optics, a rinsing pipe, a tool, or the like.

5. The endoscope according to claim 4, wherein said connecting piece is a Y-piece with an axial connection and a connection inclined thereto.

6. The endoscope according to claim 4, wherein said connecting piece comprises an axial connection and two connections inclined thereto in a Y-shaped manner, wherein said axial connection is a working connection and one of said inclined connections is an optics connection.

7. The endoscope according to claim 4, wherein an additional coupling for attaching a cannula or a working shaft with a large diameter is provided at an axial connection.

8. The endoscope according to claim 1, wherein, in a transition area to the protective pipe of said optics, the guiding pipe is provided along which the sliding piece of said adjustment means is adapted to be displaced.

9. The endoscope according to claim 1, wherein said adjustment means comprises a distance piece for length adjustment.

10. The endoscope according to claim 1, wherein said cannula is curved.

11. The endoscope according to claim 1, wherein a forceps head is attached to a distal end of said cannula, the forceps jaws of which are adapted to be actuated by means of an actuation wire guided in said cannula.

12. The endoscope according to claim 11, comprising actuation means adapted to be detachably connected with said actuation wire.

13. The endoscope according to claim 1, wherein said cannula is provided with a receiver element for a tool.

14. The endoscope according to claim 11, wherein said receiver element is attached to the distal end of said cannula.

15. The endoscope according to claim 1, comprising laser optics, the fiber strand of which is inserted in said optics cannula and a relative position of which is adapted to be adjusted with respect to a distal end of said optics cannula by means of a laser shifter.

16. The endoscope according to claim 1, wherein said optics is designed with an image sensor.

17. The endoscope according to claim 1, wherein said optics is adapted to be shifted out of said optics cannula and to be fixed.

18. The endoscope according to claim 1, comprising a brush for cleaning.

19. The endoscope according to claim 1, comprising a slightly ground trocar for insertion in said optics cannula.

20. The endoscope according to claim 1, wherein said optics has an outer diameter of approximately 0.5 mm, and wherein optics cannulas with diameters of 0.95, 1.1, 1.6, and 2.0 mm and more are provided.

21. The endoscope according to claim 1, wherein said optics comprises light and image conductors, wherein the image conductors are connected with an ocular via an ocular connection and the light conductors are connected with a light source via an illumination connection.

22. The endoscope according to claim 1, wherein the optics cannula comprises a connection, in particular a bayonet or Luer Lock connection, at the proximal end thereof.

23. The endoscope according to claim 22, wherein a working shaft is adapted to be applied at said cannula connection, said working shaft being in particular designed to accommodate a trocar.

24. The endoscope according to claim 1, wherein at least the optics cannula and a connecting piece are packed in a sterile manner.

25. A modular rigid endoscope comprising
an optics cannula manufactured from a rigid material with
optics comprising a bundle of image and light fibers guided through an interior thereof for image transmission,
wherein a distal end of said optics is provided with a lens system and seal by means of a diamond glass disk,
wherein the optics is detachably connected with the optics cannula by means of a coupling;
a plurality of disposable, sterilized cannulas or working shafts which are designed with different diameters greater than or equal to 0.5 mm, and/or connections depending on a diagnostic or therapeutic application;
an adjustment means is provided for positioning lens-side end portions of said optics with respect to a cannula/working shaft orifice, wherein said adjustment means is, on the one hand, connected with at least one of said cannulas or working shafts and, on the other hand, with said optics, said adjustment means comprising
a guiding pipe enclosing a protective pipe of said optics along which a sliding piece connected with the optics cannula is guided in a displaceable manner to position the optics and lens system within the optics cannula; and
said endoscope further comprising a protective tube for placing on an uncoated end portion of said optics during storing, transportation and decontamination,
wherein the length of the protective tube and the inner diameter of the protective tube have a diameter/length ratio so as to permit plasma sterilization and wherein said optics have an outer diameter of approximately 0.5 mm and having light conductors and image conductors.

26. The endoscope according to claim 1, wherein the optics cannula is manufactured of stainless steel.

* * * * *